United States Patent [19]

Greger et al.

[11] Patent Number: 4,994,493

[45] Date of Patent: Feb. 19, 1991

[54] N-SUBSTITUTED 5-NITROANTHRANILIC ACIDS, A PROCESS FOR THEIR PREPARATION, THEIR USE, AND PHARMACEUTICAL PRODUCTS BASED ON THESE COMPOUNDS

[75] Inventors: Rainer Greger, Heitersheim; Heinrich C. Englert; Hans-Jochen Lang, both of Hofheim am Taunus; Max Hropot, Flörsheim am Main, all of Fed. Rep. of Germany

[73] Assignees: Max-Planck-Gesellschaft zur Forderung der Wissenschaften, Gottingen; Hoechst Aktiengesellschaft, Frankfurt am Main, both of Fed. Rep. of Germany

[21] Appl. No.: 890,318

[22] Filed: Jul. 29, 1986

[30] Foreign Application Priority Data

Jul. 31, 1985 [DE] Fed. Rep. of Germany ....... 3527409
Aug. 5, 1985 [DE] Fed. Rep. of Germany ....... 3528048

[51] Int. Cl.$^5$ ............................................ A61K 31/195
[52] U.S. Cl. .................................... 514/567; 514/471; 514/438; 514/226.8; 514/237.8; 514/228.8; 514/255; 514/256; 514/247; 514/357
[58] Field of Search ............... 514/557, 567, 471, 438, 514/226.8, 255, 237.8, 256, 247, 357, 228.8; 560/21; 562/435, 453, 456, 459

[56] References Cited

PUBLICATIONS

Chem. Pharm. Bull., 27(2), p. 522.27, (1979).
J. Med. Chem., 16(2), pp. 127–130, (1973).
Indian J. Med. Res. 78, (Jul. 1983), pp. 147–150.

*Primary Examiner*—James H. Reamer
*Attorney, Agent, or Firm*—Finnegan, Henderson, Farabow, Garrett and Dunner

[57] ABSTRACT

Compounds I

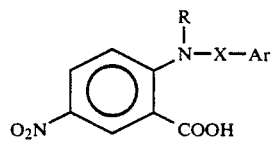

with

R equal to hydrogen or $(C_1-C_4)$-alkyl,

X equal to $(CH_2)_n$ with n = 1 – 4, unsubstituted or substituted, and

Ar is equal to an aromatic or heteroaromatic system, optionally substituted, and their pharmaceutically tolerated salts are valuable pharmaceuticals for the treatment of cerebral edema or diarrhea.

3 Claims, No Drawings

N-SUBSTITUTED 5-NITROANTHRANILIC ACIDS, A PROCESS FOR THEIR PREPARATION, THEIR USE, AND PHARMACEUTICAL PRODUCTS BASED ON THESE COMPOUNDS

The invention relates to 5-nitroanthranilic acids of the formula I

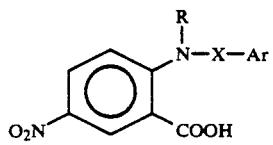

in which

R represents hydrogen or alkyl having 1-4 carbon atoms,

X represents a chain $(CH_2)_n$, n being 1, 2, 3 or 4, and the chain being unsubstituted or substituted by 1 to 2n alkyl radicals having 1-2 carbon atoms, or additionally substituted by the radical Ar, Ar being as defined below, Ar represents an aromatic or heteroaromatic system which can optionally be substituted by 1 to 3 identical or different radicals ($C_1$ or $C_2$)-alkyl, ($C_1$ or $C_2$)-alkoxy, halogen or trifluoromethyl, and to their pharmaceutically tolerated salts.

An aromatic system Ar is to be understood preferably to be phenyl, and a 5- or 6-membered heteroaromatic system Ar is preferably a radical of a 5- or 6-membered O-, N-and/or S-heterocyclic ring, in particular furyl, thienyl, isothiazolyl, oxazolyl, isoxazolyl, pyrazolyl, imidazolyl, thiazolyl, pyridyl, pyrazinyl, pyrimidinyl, pyridazinyl or triazinyl. Halogen is to be understood to be F, Cl, Br or I, preferably Cl or Br. Where compounds of the formula I have chiral carbon atoms, then the invention relates to both the S-configuration and the R-configuration at the particular center in the compounds. The compounds can then be in the form of optical isomers, of diastereoisomers, of racemates or of mixtures thereof.

Compounds similar to compounds of the formula I but having in place of the $NO_2$ group other functional groups in the various positions on the benzene nucleus are known. Pharmacological actions have been reported for, for example, 2-chloro-6-(2-phenethylamino)-benzoic acid (hypoglycemic; Chem. Pharm. Bull., 27(2), 522-7+1468-72), N-phenethylanthranilic acid (antiinflammatory; Indian J. Med. Res., 78(July), 147-50) and 5-aminosulfonyl-2-(2-(phenethylamino)-4-phenylmethylbenzoic acid (diuretic, J. Med. Chem., 16(2), 127-30).

Thus it was extremely surprising that the compounds of the formula I act to reduce the swelling of cerebral edema without at the same time having a diuretic action.

Furthermore, it was surprising that some of the compounds also have an intestinal, in particular a diarrheal or antidiarrheal, action.

The preferred compounds of the formula I a[e those in which R represents hydrogen, X represents $(CH_2)_n$ with n=2 or 3, and Ar represents the unsubstituted phenyl radical.

The invention furthermore relates to a process for the preparation of 5-nitroanthranilic acids of the formula I, which comprises A) reaction of compounds of the formula II,

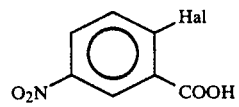

in which Hal represents Cl, F and Br, with amines of the general formula Ar—X—NRH, wherein X, R and Ar have the abovementioned meanings, B) reaction of compounds of the formula III,

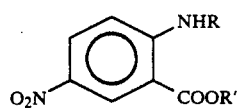

in which R has the abovementioned meaning, and in which R' represents alkyl having 1-4 carbon atoms, with compounds of the formula Z—X—Ar in which X and Ar have the abovementioned meanings and Z represents a leaving group, and elimination of the radical R' by known methods, C) reaction of compounds of the formula III, in which R and R' have the abovementioned meanings but R' additionally represents hydrogen, with compounds of the formula Ar—X'—COHal, where Ar has the abovementioned meaning and X' represents a chain $(CH_2)_{n-1}$ which can be substituted and as defined above by 1 to (2n-1) alkyl radicals and/or by the radical Ar, and in which Hal represents chlorine or bromine, to give compounds of the formula IV

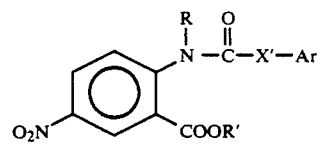

and reduction of the latter to give compounds of the formula V

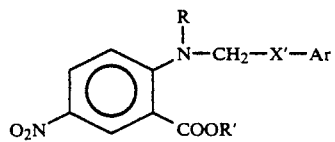

and elimination of the radical R'.

The compounds of the formula I obtained by variants A-C are converted, where appropriate, into their pharmaceutically tolerated salts.

Suitable leaving groups Z in process variant B) are all groups which can readily be nucleophilically displaced, such as, for example, halogen, tosylate, mesylate, trifluoromethanesulfonate, acetoxy or trifluoroacetoxy.

If compounds of the general formula I are prepared by process variant (A), this is advantageously carried out by reaction of the compounds of the formula II with the amines RNH—X—Ar with the addition of an acid-capture agent. In principle, all basic substances which are able to bind the HHal which is produced during the reaction are suitable, for example potassium carbonate, sodium hydroxide, sodium bicarbonate, triethylamine or, for example, an excess of the amine RNH—X—Ar. In certain circumstances, it may be an advantage to add Cu powder or Cu bronze to catalyze the reaction in the manner of an Ullmann reaction. Suitable solvents for this are all solvents which are inert towards all the reactants, such as, for example, dimethylacetamide or ethanol. It is also possible when liquid amines RNH—X—Ar are used to dispense with a solvent entirely.

Process variant (B) comprises alkylation of the aromatic amines III with the alkylating agents Z—X—Ar. This is carried out in a manner known per se such that the reactants are induced to react, where appropriate with the addition of an acid-capture agent, in an inert solvent. Dipolar aprotic solvents have proved particularly suitable for this, such as, for example, dimethylformamide or dioxane. Suitable acid-capture agents are all basic substances which are able to bind the acid liberated in the reaction, for example the bases mentioned under process variant (A). The use of potassium carbonate in dioxane has emerged as particularly advantageous for this. In general, elevated reaction temperatures are an advantage for achieving satisfactory conversions, for example the reflux temperature of dioxane. In the compounds of the formula I which have been obtained in this way the COOH group is still esterified by R'—OH. It is possible by acid- or base-catalyzed hydrolysis readily to convert these compounds by standard methods into the free anthranilic acids.

If compounds of the formula I are prepared by process variant (C), then anthranilic esters of the formula III are initially acylated by the acid halides Ar—X'—Hal. The procedure is based on standard methods for acylation reactions of this type, for example by the use of triethylamine or pyridine as acid-capture agent and of solvents which are neutral towards the reactants, such as ethyl acetate or dioxane. The subsequent reduction of the amides IV to the amines V can likewise be carried out by standard methods. It has proved particularly advantageous in this to use a reducing agent such as, for example, sodium borohydride in the presence of a Lewis acid such as boron trifluoride. The compounds V obtained from this are hydrolyzed by standard methods to give the acids of the formula I.

The compounds of the formula I, according to the invention, and their pharmaceutically tolerated salts are agents which counteract the development of a cerebral edema or can bring about or accelerate a reduction in swelling associated with this. They are administered enterally, for example orally, or parenterally (such as, for example, injection into the vascular system, for example intravenously) in doses of not less than 0.01 mg/kg, preferably 0.05 mg/kg, and in particular 0.5 mg/kg, to a maximum of 100 mg/kg, preferably 50 mg/kg, and in particular 20 mg/kg, in capsules, coated tablets, tablets or solutions with various additives. They are suitable for the treatment of cerebral edemas of various etiologies, for example edemas which develop owing to cranial traumas resulting from blunt injuries, or cerebral edemas caused by ischemia, such as, for example, following a stroke or following epileptic attacks, or as develop in association with certain brain tumors, can be treated.

EXAMPLE 1

5-Nitro-2-(3-phenylpropylamino)benzoic acid

A solution of 15.3 g of 2-chloro-5-nitrobenzoic acid and 49 g of 3-phenylpropylamine in 60 ml of dimethylacetamide is heated at 145° C. for 2 hours. After cooling, 300 ml of water are added, and the mixture is acidified (pH 2 to 1) with 2 N HCl.

The yellow crystalline precipitate is filtered off, washed several times with water, dried and recrystallized from isopropanol. Yellow crystals, melting point 178°–180° C.

EXAMPLE 2

5-Nitro-2-(2-phenylethylamino)benzoic acid

A solution of 5.6 g of 2-fluoro-5-nitrobenzoic acid and 14.5 g of 2-phenylethylamine in 20 ml of dimethylacetamide is reacted and worked up in analogy to Example 1. Yellow crystals from isopropanol, melting point 116°–118° C.

In analogy to the procedure indicated in Examples 1 and 2, it is possible to prepare, using 2-chloro- or 2-fluoro-5-nitrobenzoic acid and the appropriate amine, the compounds according to the invention which are listed below:

EXAMPLE 3

2-(2,2-Diphenylethylamino)-5-nitrobenzoic acid, melting point 232°–234° C.

EXAMPLE 4

2-(4-Phenylbutylamino)-5-nitrobenzoic acid, melting point 180°–182° C.

EXAMPLE 5

2-(1-Methyl-3-phenylpropylamino)-5-nitrobenzoic acid, melting point 228°–230° C.

EXAMPLE 6

2-(3,3-Diphenylpropylamino)-5-nitrobenzoic acid, melting point 203° C.

EXAMPLE 7

5-Nitro-2-(1-phenylethylamino)-benzoic acid (racemate and optical isomers)

EXAMPLE 8

2-(3,4,5-Trimethoxybenzylamino)-5-nitrobenzoic acid

EXAMPLE 9

2-[2-(2-Methoxyphenylethyl)amino]-5-nitrobenzoic acid

EXAMPLE 10

2-[2-(3,4-Dimethoxyphenylethyl)amino]-5-nitrobenzoic acid

EXAMPLE 11

2-[2-(4-Methoxyphenylethyl)amino]-5-nitrobenzoic acid

EXAMPLE 12

2-[2-(2-Chlorophenylethyl)amino]-5-nitrobenzoic acid

EXAMPLE 13

2-[2-(4-Chlorophenylethyl)amino]-5-nitrobenzoic acid

EXAMPLE 14

2-[2-(3-Trifluoromethylphenylethyl)amino]-5-nitrobenzoic acid

EXAMPLE 15

2-(2-Furylmethylamino)-5-nitrobenzoic acid

A solution of 14.7 g of 2-fluoro-5-nitrobenzoic acid and 23.1 g of 2-furylmethylamine in 250 ml of ethanol is boiled under a reflux condenser for 6 hours. After the solvent has been removed by distillation under reduced pressure, the residue is dissolved in 150 ml of water, the pH is adjusted to approximately 2 with 2 N HCl, and the precipitate is filtered off. After the precipitate has been washed several times with water, it is dried in a stream of air. Pale yellow crystals, melting point 190°–192° C. (from isopropanol).

EXAMPLE 16

2-Benzylamino-5-nitrobenzoic acid

EXAMPLE 17

2-(3-Phenylpropylamino)benzoic acid (a) A mixture of 14 g of 3-phenylpropyl bromide, 7.5 g of methyl anthranilate and 18 g of finely ground anhydrous potassium carbonate in 40 ml of anhydrous dioxane is boiled under a reflux condenser with a protective atmosphere of argon gas for about 60 hours, with magnetic stirring. After the solvent has been removed by distillation, 200 ml of methylene chloride and 100 ml of water are added, the organic phase is separated off and dried over magnesium sulfate, and the solvent is driven off. Column chromatography of the residue on silica gel (mobile phase toluene/methanol = 10:1) provides methyl 2-(3-phenylpropylamino)benzoate as a viscous yellow oil.

1 g of methyl 2-(3-phenylpropylamino)benzoate is heated to boiling with 5 ml of 4 N NaOH in 20 ml of methanol for 8 hours. After the solvent has been evaporated off, 5 ml of water are added to the residue, the pH is adjusted to 1 with 2 N HCl, and the precipitate is filtered off, washed with water and dried in a stream of air. Colorless crystals, melting point 103°–105° C.

(b) A mixture of 17.6 g of 3-phenylpropanoyl chloride in 40 ml of ethyl acetate is added dropwise to a solution of 15.7 g of methyl anthranilate and 21 g of triethylamine in 60 ml of methyl acetate. The mixture is stirred at room temperature for 24 hours, water is added, and the organic phase is separated off and, after the solvent has been evaporated off, methyl 2-(3-phenylpropanoylamino)benzoate is obtained as an orange-colored oil.

3.4 ml of boron trifluoride etherate are added to a solution of 5.6 g of methyl 2-(3-phenylpropanoylamino)benzoate in 35 ml of anhydrous 1,2-dimethoxyethane. After cooling to 0° C., 3.4 g of sodium borohydride are added in portions, while stirring and cooling, and then the mixture is stirred at 60° C. for 45 hours and, after cooling, is poured onto ice-water. Extraction with ethyl acetate, evaporation off of the solvent and column chromatography of the residue as described under (a) provides methyl 2-(3-phenylpropylamino)benzoate.

The methyl 2-(3-phenylpropylamino)benzoate is hydrolyzed as described under (a) to give 2-(3-phenylpropylamino)benzoic acid (melting point 103°–105° C.).

PHARMACOLOGICAL DATA

Cerebral Edema

Bilateral Temporary Cerebral Ischemia in the Mongolian Gerbil

Method:

The experiments are carried out on male Mongolian gerbils (Meriones unguiculatus; strain: Kastengrund, Hoechst AG, Frankfurt am Main) weighing 50–70 g under anesthesia. For the anesthesia, use was made of a portable anesthesia apparatus Halothane Vapor 19.1 (Drägerwerk AG, Lübeck, Federal Republic of Germany) Settings of the anesthetic gases: $O_2$ 1.1 1/min + $N_2$ 2.0 1/min + halothane 3.2% by volume until the tolerance stage is reached. The inhaled halothane gas mixture is passed into a small desiccator in which the animals remain until the tolerance stage is reached. The animals are then removed from the desiccator, immobilized on an operating stage for rats and the anesthesia is continued via a breathing mask with a halothane concentration of 1.2% by volume or less. Then both common carotid arteries are exposed with minimum damage and are occluded with microvessel clips for 20 min. Thereafter, recirculation is carried out for 90 min. After occlusion of the vessels, the animals are placed in observation jars whose bases have been brought to a temperature of about 29° C. by use of heating pads. The animals are observed in the glass vessels for 110 min, recording the neurological signs in accordance with a classification system. The test substances are administered orally in a volume of 5 ml/kg body weight before the vessel occlusion. The control animals received the same volume of the relevant vehicle. After an observation period of 110 min, the animals are decapitated under anesthesia, and the brains are removed. The cerebellum is discarded, and the wet weight of both halves of the brain is determined.

The weighed brains are dried in a drying oven at 95° C. for 2 days. After the dry weight has been determined, the degree of cerebral edema is calculated as the percentage water content.

References

1. Levy, D. E. and T. E. Duffy: J. Neurochem. 28:63, 1977
2. Welsh, F. A. and W. Rieder: J. Neurochem. 31:299,
3. Cain, A. P. and M. E. Corcoran: Electroenceph. Clin. Neurophys. 49:360, 1980

Effect on cerebral edema in the gerbil at an oral dose of 100 mg/kg.

| Product | Dose | % Water content of the brain x ± SD |
|---|---|---|
| sham-operated control (n = 5) | vehicle (2% by volume starch solution) | 79.59 ± 0.11 |
| cerebral edema control (n = 5) | vehicle | 80.60 ± 0.06 |
| 5-nitro-2-(3-phenylpropyl-amino)benzoic acid (n = 6) | 100 mg/kg oral (suspended in vehicle) | 80.45 ± 0.07 |

SD = standard deviation

We claim:

1. A pharmaceutical composition for the treatment of cerebral edema which comprises an effective amount of a compound of the formula I

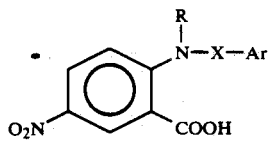

in which

R is hydrogen or $(C_1-C_4)$alkyl,

X is a chain $(CH_2)_n$, n being 1, 2, 3 or 4, which chain is unsubstituted or substituted by 1 to 2n $(C_1-C_2)$alkyl radicals, it being additionally possible for the chain to be substituted by a radical Ar which is as defined below, and Ar is selected from the group consisting of phenyl, furyl, thienyl, isothiazolyl, oxazolyl, isoxazolyl, pyrazolyl, imidazolyl, thiazolyl, pyridyl, pyrazinyl, pyrimidinyl, pyridazinyl and triazinyl, said radical being unsubstituted or substituted by 1 to 3 identical or different radicals selected from the group consisting of $(C_1-C_2)$-alkyl, $(C_1-C_2)$alkoxy, F, Cl, Br, I and $CF_3$, or a pharmaceutically tolerated salt thereof together with a pharmaceutically acceptable carrier.

2. A method for treating cerebral edema comprising administering to a host in need of said treatment an effective amount of a compound of the formula I

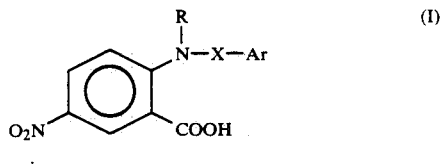

in which

R is hydrogen or $(C_1-C_4)$alkyl,

X is a chain $(CH_2)_n$, n being 1, 2, 3 or 4, which chain is unsubstituted or substituted by 1 to 2n $(C_1-C_2)$alkyl radicals, it being additionally possible for the chain to be substituted by a radical Ar which is as defined below, and Ar is selected from the group consisting of phenyl, furyl, thienyl, isothiazolyl, oxazolyl, isoxazolyl, pyrazolyl, imidazolyl, thiazolyl, pyridyl, pyrazinyl, pyrimidinyl, pyridazinyl and triazinyl, said radical being unsubstituted or substituted by 1 to 3 identical or different radicals selected from the group consisting of $(C_1-C_2)$-alkyl, $(C_1-C_2)$alkoxy, F, Cl, Br, I and $CF_3$, or a pharmaceutically tolerated salt thereof.

3. A method for preparing the pharmaceutical composition of claim 1 for the treatment of cerebral edema.

* * * * *